United States Patent [19]

O'Brien et al.

[11] Patent Number: 5,232,278
[45] Date of Patent: Aug. 3, 1993

[54] LATCHING MECHANISM FOR INSTRUMENT DELIVERY SYSTEMS

[75] Inventors: James O'Brien, Dublin; Leonard Kelly, Norristown; Jack Wilbert, Devon, all of Pa.

[73] Assignee: Isell/Diversatronics, Inc., Norristown, Pa.

[21] Appl. No.: 885,545

[22] Filed: May 19, 1992

[51] Int. Cl.⁵ .............................................. A47B 88/00
[52] U.S. Cl. .................................. 312/319.1; 312/333; 292/DIG. 63
[58] Field of Search .................... 312/333, 9.22, 319.1, 312/334.11, 215; 292/227, DIG. 37, DIG. 63

[56] References Cited

U.S. PATENT DOCUMENTS

| | | | |
|---|---|---|---|
| 1,700,299 | 1/1929 | Wolters | 292/127 X |
| 2,728,626 | 12/1955 | Gussack | 312/333 |
| 3,000,686 | 9/1961 | Kobitter | 312/333 |
| 4,653,820 | 3/1987 | Tazaki | 312/333 |

Primary Examiner—Rodney M. Lindsey
Attorney, Agent, or Firm—Staas & Halsey

[57] ABSTRACT

A latching mechanism for an instrument delivery system having a base, a slide tray, movable relative to the base between an opened position and a closed position, wherein the latching mechanism comprises: an actuating unit, including a push button mounted on the slide tray, for moving a member from a first position to a second position in response to movement of the push button from an extended position to a depressed position; and a latching unit for latching the slide tray in at least one of the opened position and the closed position when the member is in the first position and for unlocking the slide tray when the member is in the second position.

8 Claims, 3 Drawing Sheets

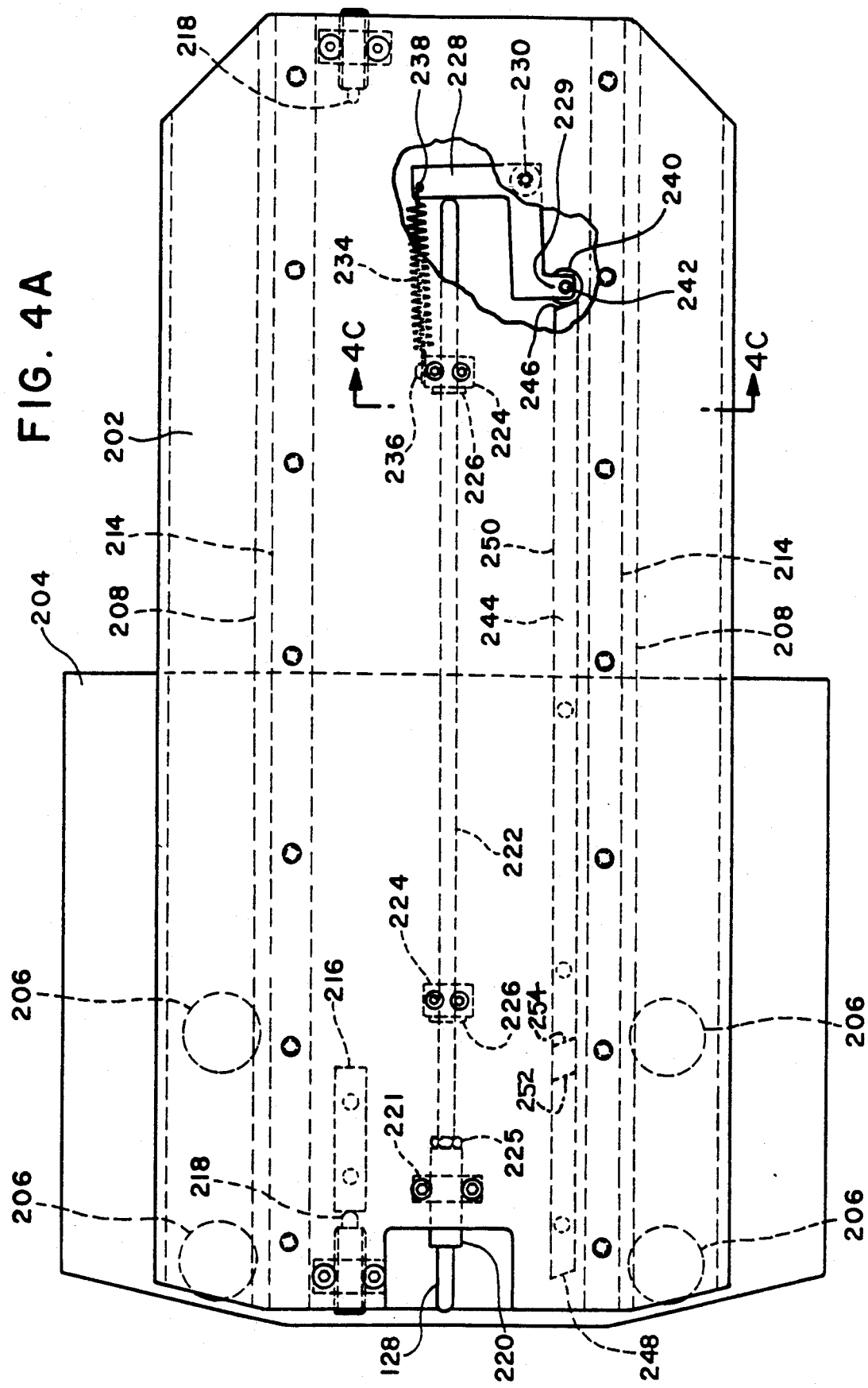

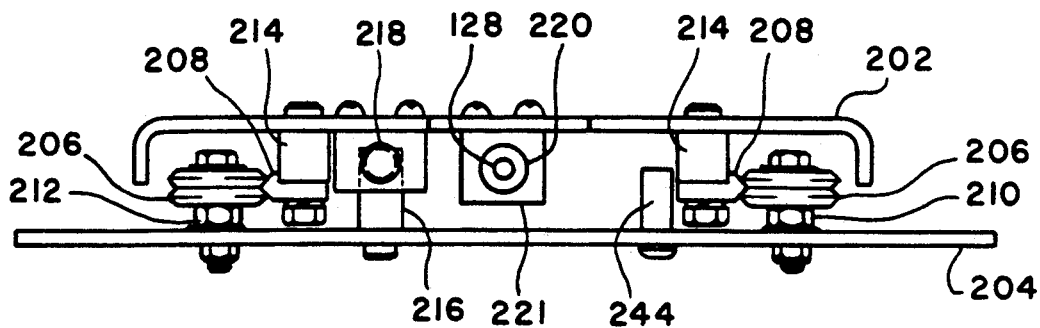
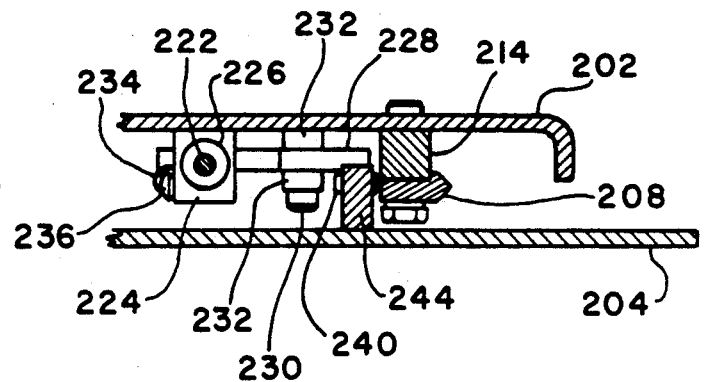
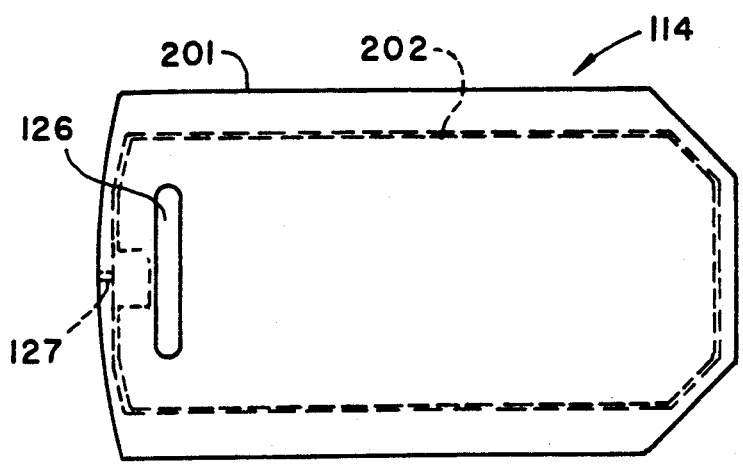
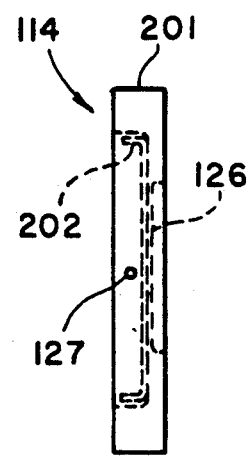

LATCHING MECHANISM FOR INSTRUMENT DELIVERY SYSTEMS

BACKGROUND OF THE INVENTION

1. Field of the Invention

The present invention relates to instrument delivery systems and, more particularly, to a latching mechanism for instrument delivery systems.

2. Description of the Related Art

Instrument delivery systems are used to deliver instruments to a position where they are used. For example, instrument delivery systems are used in ophthalmologic examinations, where several instruments are used to examine a patient.

FIG. 1 shows a conventional instrument delivery system 10. Conventional instrument delivery system 10 includes a circular table 12, which is rotatable about its central axis and which includes a locking mechanism (not shown) for locking rotation of circular table 12 at 90° increments. Circular table 12 also includes slide trays 14a–14d, which slide between an opened position and a closed position. Slide tray 14a is shown in FIG. 1 in its opened position, while slide trays 14b–14d are shown in their closed positions. Instruments 16a–16d are respectively supported on slide trays 14a–14d. Electrical power outlets (not shown) are provided on each of slide trays 14a–14d to provide power to instruments 16a–16d, if required.

A patient's chair 18 and an operator's chair 20 are positioned on opposite sides of one of slide trays 14a–14d, with circular table 12 locked in one of its 90° interval positions. Typically, the operator seated in chair 20 rotates circular table 12 to a position such as that shown in FIG. 1, where a selected one of slide trays 14a–14d is located between patient's chair 18 and operator's chair 20 and where circular table 12 is locked by the locking mechanism (not shown) in one of its 90° interval positions. Then, the operator pulls the selected one of the slide trays 14a–14d, i.e., slide tray 14a in FIG. 1, into its opened position, and examines the patient seated in chair 18 using instrument 16a. After examination is completed using instrument 16a, the operator pushes slide tray 14a to its closed position, and rotates circular table 12 to another 90° interval position. Consequently, any desired instrument 16a–16d can be delivered to an examination position between patient's chair 18 and operator's chair 20 by rotating circular table 12 to a selected 90° interval position and pulling the selected one of the slide trays 14a–14d to its opened position.

Typically, conventional instrument delivery system 10 includes a latching mechanism (not shown) for latching and unlatching slide trays 14a–14d in their opened and closed positions. For example, one type of conventional instrument delivery system includes a lever-actuated latching mechanism in each of the slide trays 14a–14d. These lever-actuated latching mechanisms are actuated by levers 22a–22d, which are centrally located on the ends of slide trays 14a–14d. The operation of these lever-actuated latching mechanisms is undesirably noisy and unreliable because the operator is often uncertain of the direction in which levers 22a–22d must be pushed for actuation.

Other conventional instrument delivery systems use remotely-actuated latching mechanisms actuated by remote push buttons 24a–24d. However, remote push buttons 24a–24d require a dedicated left or right hand operation. That is, as shown in FIG. 1, in order to unlatch opened slide tray 14a, the operator must be on the side of slide tray 14a where remote push button 24a is located. Consequently, the operator may be in an inconvenient location for actuating remote push button 24a.

SUMMARY OF THE INVENTION

It is an object of the present invention to provide an improved latching mechanism for an instrument delivery system that quietly and reliably latches and unlatches a sliding tray of the instrument delivery system.

It is another object of the present invention to provide an improved latching mechanism for an instrument delivery system that can be actuated from either side of a slide tray of the instrument delivery system, without requiring dedicated left or right hand operation.

In order to achieve the foregoing and other objects, in accordance with the purposes of the present invention as described herein, a latching mechanism for an instrument delivery system having a base and a slide tray movable relative to the base between an opened position and a closed position, the latching mechanism comprises: an actuating unit, including a push button mounted on the slide tray, for moving a member from a first position to a second position in response to an operator depressing the push button; and a latching unit for latching the slide tray in at least one of the opened position and the closed position when the member is in the first position and for unlatching the slide tray when the member is in the second position.

These and other features and advantages of the present invention will become more apparent with reference to the following detailed description and drawings. However, the drawings and descriptions are merely illustrative in nature and not restrictive.

BRIEF DESCRIPTION OF THE DRAWINGS

The accompanying drawings illustrate several aspects of the present invention, and together with the descriptions serve to explain the principles of the present invention. Like reference numerals denote like elements. In the drawings:

FIGS. 3A and 3B are respectively top and front views of a slide tray according to the present invention; and FIGS. 4A–4C are respectively top, front and sectional views of a latching mechanism according to the present invention.

DETAILED DESCRIPTION OF THE PREFERRED EMBODIMENTS

Figure 1:
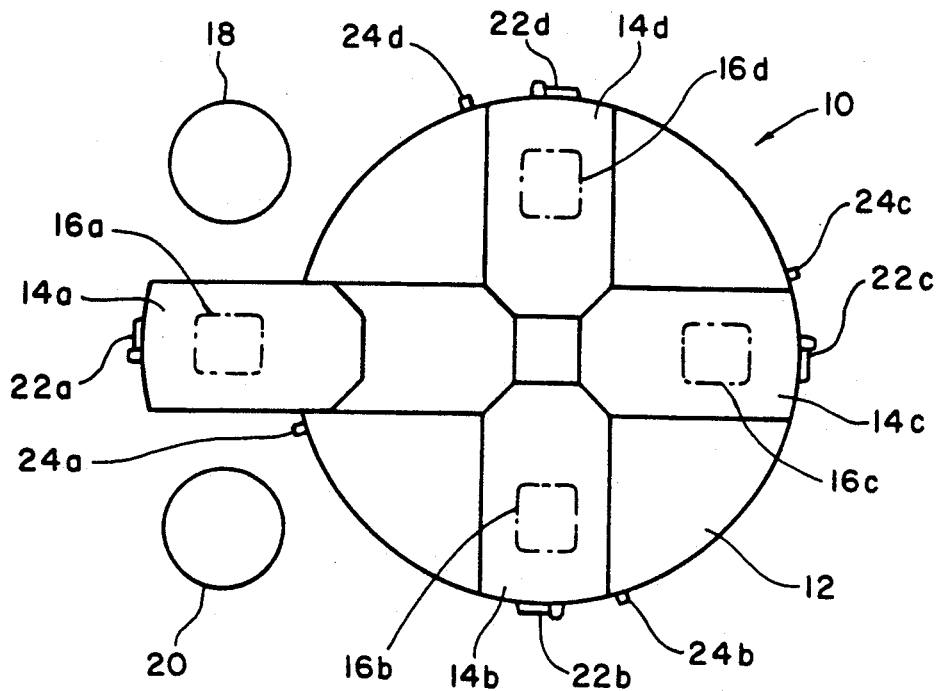
FIG. 1 is a top view of a conventional instrument delivery system.
Figure 2:
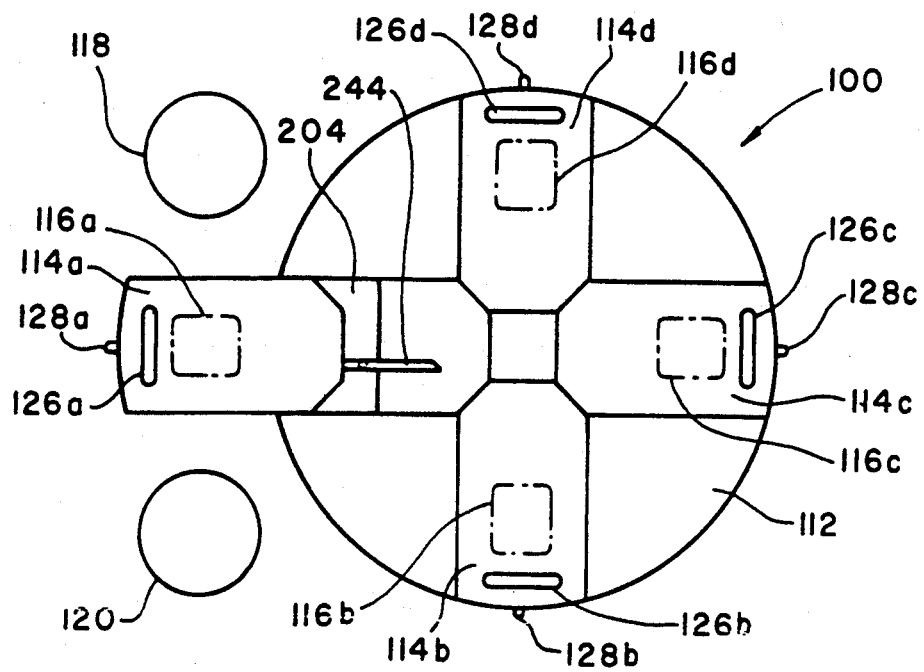
FIG. 2 is a top view of an instrument delivery system according to the present invention.

FIG. 2 shows a top view of an instrument delivery system 100 according to the present invention. As in a conventional instrument delivery system, instrument delivery system 100 includes a base 112, which is rotatable about its central axis. Base 112 includes a conventional locking mechanism (not shown) for locking rotation of base 112 at 90° interval positions. Slide trays 114a–114d each slide between an opened position and a closed position. Slide tray 114a is shown in FIG. 2 in its opened position, while slide trays 114b–114d are shown in their closed positions. Instruments 116a–116d are respectively supported on slide trays 114a–114d. Electrical power outlets (not shown) are provided on each of slide trays 114a-114d in order to provide power to instruments 116a-116d, if required.

Base 112 need not be circular. For example, base 112 may have an octagonal shape. Further, base 112 may have any number of slide trays 114. For example, base 112 may include eight slide trays and, consequently, include a locking mechanism for locking rotation of base 112 at 45° interval positions.

Chairs 118 and 120 are positioned on opposite sides of one of slide trays 114a-114d, with base 112 locked in one of its 90° interval positions. The operator, seated in either chair 118 or 120, rotates base 112 to a 90° interval position, such as that shown in FIG. 2, where a selected one of slide trays 114a-114d is located between chairs 118 and 20 and where rotation of base 112 is locked by the conventional locking mechanism. Then, the operator actuates a latching mechanism, discussed below, and pulls the selected one of the slide trays 114a-114d, i.e., slide tray 114a in FIG. 2, into its opened position. The operator then examines the patient seated in the other of chairs 118 and 120 using instrument 116a. After examination is completed using instrument 116a, the operator again actuates the latching mechanism and pushes slide tray 114a to its closed position and rotates base 112 to another 90° interval position. Consequently, any desired instrument 116a-116d can be delivered to an examination position between chairs 118 and 120 by rotating base 112 to a selected 90° interval position, actuating the latching mechanism and pulling the selected one of trays 114a-114d to its opened position.

As shown in FIG. 2, slide trays 114a-114d respectively include centrally located recessed handles 126a-126d and push buttons 128a-128d.

To unlatch the desired slide tray 114 from its opened or closed position the operator depresses its push button 128, thereby actuating the latching mechanism, discussed below. The operator's fingers are placed in recessed handle 126 and the operator's thumb is used to depress push button 128. With the operator's fingers in recessed handle 126, slide tray 114 can be easily pulled open. Consequently, recessed handle 126 and push button 128 provide one-handed operation Because each push button 128 is centrally located on a slide tray 114, dedicated left or right hand operation is not required and, consequently, the operator is always in a convenient location for actuating the latching mechanism of the present invention, i.e., the user may actuate the latching mechanism while seated on either side of the slide tray 114.

FIGS. 3A and 3B respectively show top and front views of slide tray 114 according to the present invention. Slide tray 114 includes a cover 201 made of, for example, molded fiberglass. Cover 201 includes a hole 127, through which push button 128 (not shown in FIGS. 3A and 3B) extends, and also includes recessed handle 126. Molded fiberglass is preferred because it is aesthetically pleasing and because of the ease in which recessed handle 126 and hole 127 may be incorporated within cover 201. A top plate 202 is attached to cover 201 by, for example, attachment screws (not shown) or adhesive. Top plate 202 may be made of a structurally stiff material, for example, steel. Alternatively, cover 201 and top plate 202 may be integrally formed of the same material, for example, steel.

FIGS. 4A-4C respectively show top, front and sectional views of a latching mechanism according to the present invention. Top plate 202 is shown in FIGS. 4A-4C with cover 201 removed for the sake of simplicity. A base plate 204 is attached to base 112 (not shown in FIGS. 4A-4C) by, for example, mounting screws (not shown). Base plate 204 may be made of a structurally stiff material, for example, steel. Base 112 may be made of an aesthetically pleasing and durable material, for example, high pressure laminate. Alternatively, base plate 204 and base 112 may be integrally formed of the same material, for example, steel.

Top plate 202 is slidably mounted relative to base plate 204 by, for example, a V-wheel/track arrangement. V-wheels 206 are mounted on base plate 204 by nuts and bolts, for example. Tracks 208 are mounted on top plate 202 by nuts and bolts, for example. V-wheels 206 engage tracks 208 and rotate as top plate 202 slides relative to base plate 204. Fixed bushing spacers 210 are used to fixedly position the V-wheels 206 that engage one of tracks 208. Adjustable bushing spacers 212 are used to adjustably position the V-wheels 206 that engage the other one of tracks 208. Track spacers 214 are mounted between tracks 208 and top plate 202.

A stop block 216 is mounted on base plate 204 by, for example, bolts. Conventional spring plungers 218 are mounted on top plate 202 by, for example, screws. Spring plungers 218 include a fixed base portion and a movable plunger portion, and are mounted on top plate 202 so that the movable plunger portion engages stop block 216 when slide tray 114 is in its open position and closed position, respectively. The movable plunger portion of each spring plunger 218 is biased by an internal spring (not shown) so that slide tray 114 is biased toward its opened position when slide tray 114 is in its closed position, and vice-versa. Spring plungers 218 may be, for example, Model No. S60, VLIER Engineering, Watertown, MA.

Push button 128 is a movable plunger portion of a conventional switch plunger 220. Switch plunger 220 may be, for example, Model No. V12AA05, BACO Controls, Inc., Cazerovia, NY. The fixed base portion of switch plunger 220 is attached to top plate 202 by a mount block 221 and mounting screws. Push button 128 is spring biased relative to the base of switch plunger 220 by an internal spring (not shown). Push button 128 has a depressed and extended position. In the depressed position, the internal end (not shown) of push button 128 extends about one-fourth inch deeper into the fixed base portion of switch plunger 220 than in the extended position One end (not shown) of a latch release rod 222 extends into the fixed base portion of switch plunger 220 and engages the internal end (not shown) of push button 128. Latch release rod 222 is slidably received in bearing blocks 224 which are attached to top plate 202 by, for example, mounting screws. The end of latch release rod 222 may be threaded so as to receive a jam nut 225, which engages the end of the fixed base portion of switch plunger 220 when push button 128 is in the extended position Bearing blocks 224 include annular bearings 226 made of nylon, for example, so that latch release rod 222 easily slides therethrough.

A latch lever 228 is pivotably attached to top plate 202 by a pivot bolt 230, for example. Latch lever 228 is spaced from pivot bolt 230 and top plate 202 by nylon spacers 232. Latch lever 228 is substantially L-shaped A first end of latch lever 228 is biased into engagement with latch release rod 222 by a spring 234. One end of spring 234 is attached to a bearing block 224 by, for example, a screw 236. The other end of spring 234 is connected to latch lever 228 by, for example, a pin 238. Spring 234 may be, for example, an extension type having closed loops.

Latch lever 228 includes a projection 229 on which a ball bearing roller 240 is rotatably mounted by a pin 242. Ball bearing roller 240 may be, for example, model number R-3HH, New Hampshire Ball Bearing, Inc., Chatsworth, CA. A latch stop bar 244 is mounted to base plate 204 by, for example, mounting screws. The ends of latch stop bar 244 include tapered edges 246 and 248, and side edge 250. Tapered edges 246 and 248 are inclined at about 15° from a direction perpendicular to the direction of motion of slide tray 114 between the opened and closed positions.

When slide tray 114 is in the closed position, ball bearing roller 240 latchingly engages tapered edge 246. Consequently, slide tray 114 cannot be moved toward the opened position because ball bearing roller 240 is in engagement with tapered edge 246. In addition, slide tray 114 is biased toward the opened position because the movable plunger portion of spring plunger 218 is in contact with stop block 216.

When push button 128 is pressed into its depressed position while slide tray 114 is in the closed position, latch release rod 222 slides toward latch lever 228 against the spring biases of switch plunger 220 and spring 234. Consequently, latch lever 228 rotates clockwise (relative to FIG. 4A) about pivot bolt 230 until ball bearing roller 240 no longer contacts tapered edge 246 of latch stop bar 244. Slide tray 114 is thereby unlatched from the closed position. As the operator pulls slide tray 114 to the opened position, ball bearing roller 240 rolls along side edge 250, until ball bearing roller 240 engages tapered edge 248.

When ball bearing roller 240 engages tapered edge 248 of latch stop bar 244, slide tray 114 is latched in the opened position. In the opened position, slide tray 114 is biased against movement toward the closed position because ball bearing roller 240 is engaged with tapered edge 248 and latch lever 228 is biased against clockwise (relative to FIG. 4A) rotation by spring 234. Likewise, when slide tray 114 is in the opened position, slide tray 114 is biased toward the closed position because the movable plunger portion of spring plunger 218 is engaged with stop block 216. Consequently, slide tray 114 is latched in the opened position.

When push button 128 is pressed into its depressed position while slide tray 114 is in the opened position, latch release rod 222 slides toward latch lever 228 against the spring biases of switch plunger 220 and spring 234. Consequently, latch lever 228 is rotated clockwise (relative to FIG. 4A) and ball bearing roller 240 moves out of engagement with tapered edge 248. Then, the operator pushes side tray 114 toward the closed position, and ball bearing roller 240 rides along side edge 250 until it engages tapered edge 246 to thereby latch slide tray 114 in the closed position.

Also, the present invention may be modified to latch the slide tray at one or more intermediate positions between the opened position and the closed position by including intermediate tapered edges 252 and 254 (shown in phantom lines in FIG. 4A) in latch stop bar 244. Intermediate tapered edges 252 and 254 are inclined at about 15° from a direction perpendicular to the direction of motion of slide tray 114 between the opened and closed positions. In addition, intermediate tapered edges 252 and 254 are spaced relative to one another so that ball bearing roller 240 fits therebetween.

When slide tray 114 is in the intermediate position, ball bearing roller 240 is latchingly engaged between intermediate tapered edges 252 and 254. Consequently, slide tray 114 cannot be moved toward the opened position because ball bearing roller 240 is in engagement with intermediate tapered edge 252. In addition, slide tray 114 cannot be moved toward the closed position because ball bearing roller 240 is in engagement with intermediate tapered edge 254. When push button 128 is pressed into its depressed position while slide tray 114 is in the intermediate position, latch release rod 222 slides toward latch lever 228 against the spring biases of switch plunger 220 and spring 234. Consequently, latch lever 228 rotates clockwise (relative to FIG. 4A) and ball bearing roller 240 moves out of engagement with intermediate tapered edges 252 and 254. Then, as the operator either pulls slide tray 114 toward the opened position or pushes slide tray 114 toward the closed position, ball bearing roller 240 rolls along side edge 250.

According to the present invention, the operation of the latching mechanism is reliable since no electricity is required and since actuation is easily understood and requires little effort and movement. Also, because the latching mechanism according to the present invention is actuated by a push button that is centrally located on the slide tray, dedicated left or right hand operation is not required. In addition, operation of the latching mechanism according to the present invention is quieter than conventional latching mechanisms.

Numerous modifications and adaptations of the present invention will be apparent to those so skilled in the art. For example, the present invention may be modified to substitute various other mechanical linkages connected to a push button mounted on a slide tray. In addition, the present invention may be modified to include electrical actuation, e.g., a solenoid electrically connected to an electrical push button mounted on a slide tray. Thus, it is intended by the following claims to cover all modifications and adaptations which fall within the true spirit and scope of the present invention.

What is claimed is:

1. A latching mechanism for an instrument delivery system having a base, a slide tray, and means for moving the slide tray relative to the base between an opened position and a closed position, said latching mechanism comprising:

actuating means, including a push button mounted on the slide tray, for moving a member from a first position to a second position in response to movement of said push button from an extended position to a depressed position, wherein said actuating means further includes a latch release rod slidably attached to the slide tray and having a first end cooperatively engaged with said push button, said latch release rod being slidable between a third position and a fourth position in response to movement of said push button between said extended position and said depressed position, respectively, a latch lever pivotably attached to the slide tray, said member being mounted on said latch lever, and biasing means for biasing said latch lever into cooperative engagement with a second end of said latch release rod so that said latch lever pivots between a fifth position and a sixth position in response to the sliding motion of said latch release rod between said third position and said fourth position, respectively;

latching means for latching the slide tray in at least one of the opened position and the closed position when said member is in said first position and for unlatching the slide tray when said member is in said second position's aid latching means includes a latch stop bar mounted on the base, said latch stop bar having at least one tapered edge; and said latch lever being arranged so that said member is in said first position and contacts said tapered edge when said latch lever is in said fifth position and so that said member is in said second position and disengaged from said tapered edge when said latch lever is in said sixth position.

2. A latching mechanism as recited in claim 1, wherein:

said member is a roller rotatably mounted on said latch lever.

3. A latching mechanism for an instrument delivery system having a base, a slide tray, and means for moving the slide tray relative to the base between an opened position and a closed position, said latching mechanism comprising:

actuating means, including a push button mounted on the slide tray, for moving a member from a first position in response to movement of said push button from an extended position to a depressed position;

latching means for latching the slide tray in at least one of the opened position and the closed position when said member is in said first position and for unlatching the slide tray when said member is in said second position; and stop means for urging the slide tray toward the opened position when the slide tray is in the closed position and for urging the slide tray toward the closed position when the slide tray is in the opened position.

4. A latching mechanism as recited in claim 3, wherein said stop means includes:

a stop block mounted on the base;

a first spring plunger mounted on the slide tray and positioned to engage said stop block and bias the slide tray toward the closed position when the slide tray is in the opened position; and a second spring plunger mounted on the slide tray and positioned to engage said stop block and bias the slide tray toward the opened position when the slide tray is in the closed position.

5. A latching mechanism for an instrument delivery system having a base and a slide tray movable relative to the base between an opened position and a closed position, said latching mechanism comprising:

a push button movable between an extended position and a depressed position, said push button being mounted on the slide tray;

a latch release rod slidably attached to the slide tray and having a first end cooperatively engaged with said push button, said latch release rod being slidable between a first position and a second position in response to movement of said push button between said extended position and said depressed position, respectively;

a latch lever pivotably attached to the slide tray;

a spring having a first end attached to the slide tray and a second end attached to said latch lever so as to bias said latch lever into engagement with a second end of said latch release rod so that said latch lever pivots between a third position and a fourth position in response to the sliding motion of said latch release rod between said first position and said second position, respectively;

a roller rotatably mounted on said latch lever so as to move between a fifth position and a sixth position in response to the pivoting motion and a sixth position in response to the pivoting motion of said latch lever between said third position and said fourth position, respectively;

a latch stop bar mounted on the base and having a major edge and a minor edge; and said latch lever being arranged so that said roller is in said fifth position and contacts said minor edge when the slide tray is in one of the opened position and the closed position.

6. A latching mechanism as recited in claim 5, wherein:

said latch lever being arranged so that when said roller is in said sixth position said roller is disengaged from said minor edge.

7. A latching mechanism as recited in claim 5, wherein:

said latch lever being arranged so that said roller engages said major edge when the slide tray is in a position between the opened position and the closed position.

8. A latching mechanism as recited in claim 5, wherein:

said minor edge is inclined about 15° from a direction perpendicular to the direction of motion of said slide tray between the opened position and the closed position.

* * * * *

UNITED STATES PATENT AND TRADEMARK OFFICE
CERTIFICATE OF CORRECTION

PATENT NO. : 5,232,278
DATED : August 3, 1993
INVENTOR(S) : James O'Brien et al.

It is certified that error appears in the above-indentified patent and that said Letters Patent is hereby corrected as shown below:

Col. 3, line 16, "20" should read --120--.

Col. 4, line 48, "position" should be --position.--.

Col. 7, line 7, "position's aid" should be
--position, said--.

Signed and Sealed this

Twenty-sixth Day of July, 1994

Attest:

BRUCE LEHMAN

Attesting Officer    Commissioner of Patents and Trademarks